(12) United States Patent
Han et al.

(10) Patent No.: US 6,191,298 B1
(45) Date of Patent: Feb. 20, 2001

(54) THIOALKENYLPHOSPHONIC ACID ESTER AND PROCESS FOR THE PREPARATION THEREOF

(75) Inventors: Li-Biao Han; Masato Tanaka, both of Tsukuba (JP)

(73) Assignee: Agency of Industrial Science and Technology (JP)

( * ) Notice: Under 35 U.S.C. 154(b), the term of this patent shall be extended for 0 days.

(21) Appl. No.: 09/521,844

(22) Filed: Mar. 9, 2000

(30) Foreign Application Priority Data

May 26, 1999 (JP) .................................................. 11-146135

(51) Int. Cl.$^7$ ....................................................... C07F 9/40

(52) U.S. Cl. ........................... 558/161; 558/142; 558/187

(58) Field of Search ..................................... 558/142, 161, 558/187

(56) References Cited

U.S. PATENT DOCUMENTS 3,584,084 * 6/1971 Brown .................................. 558/187

* cited by examiner

*Primary Examiner*—Michael G. Ambrose
(74) *Attorney, Agent, or Firm*—Lorusso & Loud

(57) ABSTRACT

A phosphonic acid ester compound of the formula:

$$R^1C(SR^3)=CHP(=O)(OR^2)_2$$

or $$[P(=O)(OR^2)_2]CH=C(SR^3)—R^4—C(SR^3)=CH[P(=O)(OR^2)_2]$$

wherein $R^1$ represents a monovalent group selected from hydrogen, alkyl, cycloalkyl, cycloalkenyl, aryl, aralkyl, alkenyl and silyl, $R^2$ and $R^3$ each represent aryl and $R^4$ represents alkylene or cycloalkylene. The ester compound is produced by reaction of an acetylene compound, $R^1C\equiv CH$ or $HC\equiv C—R^4—C\equiv CH$, with with a phosphorothioate, $(R^2O)_2P(=O)SR^3$, in the presence of a palladium complex catalyst.

4 Claims, No Drawings

THIOALKENYLPHOSPHONIC ACID ESTER AND PROCESS FOR THE PREPARATION THEREOF

BACKGROUND OF THE INVENTION

This invention relates to a thioalkenyl phosphonic acid ester and to a process for the preparation thereof.

Thioalkenyl phosphonic esters are a group of compounds useful as intermediate compounds for the production of fine chemicals, because they can easily give, by Michael reaction with a nucleophile, a carbanion which in turn causes Horner-Emmons addition reaction with a carbonyl compound and because they can undergo a carbon—carbon bond-forming reaction by regio- or stereo-selective coupling with a vinyl halide, an aryl halide or Grignard reagent in the presence of a transitional metal catalyst.

At present, no methods have been known which can produce thioalkenyl phosphonic esters by a single stage reaction of a hydrocarbon. A reaction of a thioalkenyl halogen compound with a secondary phosphite under basic conditions may yield a thioalkenyl phosphonic ester. An addition of a secondary phosphite to a thioalkyne may also produce a thioalkenyl ether. These methods, however, are not advantageous from the industrial point of view, because the sulfur-containing raw materials are not easily obtainable.

SUMMARY OF THE INVENTION

It is, therefore, an object of the present invention to provide a simple process which can produce a thioalkenyl phosphonic ester at low costs using an easily feasible starting material.

Another object of the present invention is to provide a novel thioalkenyl phosphonic ester.

In accordance with one aspect of the present invention, there is provided a process for the preparation of a thioalkenylphosphonic acid ester of the following formula (I):

$$R^1C(SR^3)=CHP(=O)(OR^2)_2 \qquad (I)$$

wherein $R^1$ stands for a monovalent group selected from hydrogen atom, an alkyl group, a cycloalkyl group, a cycloalkenyl group, an aryl group, an aralkyl group, an alkenyl group and a silyl group, $R^2$ stands for an aryl group and $R^3$ stands for an aryl group, comprising reacting an acetylene compound of the following formula (II):

$$R^1C\equiv CH \qquad (II)$$

wherein $R^1$ is as defined above, with a phosphorothioate of the following formula (III):

$$(R^2O)_2P(=O)SR^3 \qquad (III)$$

wherein $R^2$ and $R^3$ are as defined above, in the presence of a palladium complex catalyst.

In another aspect, the present invention provides a process for the preparation of a bis(thioalkenyl)phosphonic acid ester of the following formula (IV):

$$[P(=O)(OR^2)_2]CH=C(SR^3)-R-C(SR^3)=CH[P(=O)(OR^2)_2] \qquad (IV)$$

wherein $R^2$ stands for an aryl group, $R^3$ stands for an aryl group and $R^4$ stands for an alkylene group or a cycloalkylene group, comprising reacting an acetylene compound of the following formula (II):

$$HC\equiv C-R^4-C\equiv CH \qquad (V)$$

wherein $R^4$ is as defined above, with a phosphorothioate of the following formula (III):

$$(R^2O)_2P(=O)SR^3 \qquad (III)$$

wherein $R^2$ and $R^3$ are as defined above, in the presence of a palladium complex catalyst.

The present invention also provides a thioalkenylphosphonic acid ester of the following formula (I):

$$R^1C(SR^3)=CHP(=O)(OR^2)_2 \qquad (I)$$

wherein $R^1$ stands for a monovalent group selected from hydrogen atom, an alkyl group, a cycloalkyl group, a cycloalkenyl group, an aryl group, an aralkyl group, an alkenyl group and a silyl group and $R^2$ stands for an aryl group and $R^3$ stands for an aryl group.

The present invention further provides a bis(thioalkenyl) phosphonic acid ester of the following formula (IV):

$$[P(=O)(OR^2)_2]CH=C(SR^3)-R^4-C(SR^3)=CH[P(=O)(OR^2)_2] \qquad (IV)$$

wherein $R^4$ stands for an aryl group, $R^3$ stands for an aryl group and R stands for an alkylene group or a cycloalkylene group.

Other objects, features and advantages of the present invention will become apparent from the detailed description of the preferred embodiments of the invention to follow.

DETAILED DESCRIPTION OF THE PREFERRED EMBODIMENTS OF THE INVENTION

The phosphorothioate used as a raw material in the process of the present invention is represented by the formula (III):

$$(R^2O)_2P(=O)SR^3 \qquad (III)$$

wherein $R^2$ and $R^3$ each stand for an aryl group preferably having 6–14 carbon atoms, more preferably 6–12 carbon atoms. Illustrative of suitable aryl groups are phenyl, tolyl and napththyl.

The phosphorothioate is reacted with an acetylene compound of the formula (II) or (V)

$$R^1C\equiv CH \qquad (II)$$

$$HC\equiv C-R^4-C\equiv CH \qquad (V)$$

wherein $R^1$ stands for a monovalent group selected from (a) hydrogen atom,
(b) an alkyl group preferably having 1–18 carbon atoms, more preferably 1–10 carbon atoms, such as methyl, ethyl, propyl, butyl, hexyl octyl or decyl,
(c) a cycloalkyl group preferably having 5–18 carbon atoms, more preferably 5–10 carbon atoms, such as cyclohexyl, cyclooctyl or cyclododecyl,
(d) a cycloalkenyl group preferably having 5–18 carbon atoms, more preferably 5–10 carbon atoms, such as cyclohexenyl, cyclooctenyl or cyclododecenyl,
(e) an aryl group preferably having 6–14 carbon atoms, more preferably 6–10 carbon atoms, such as phenyl, naphthyl, substituted phenyl (e.g. tolyl or benzylphenyl) or substituted naphthyl (e.g. methylnaphthyl),
(f) an aralkyl group preferably having 7–13 carbon atoms, more preferably 7–9 carbon atoms, such as benzyl, phenethyl, phenylbenzyl, naphthylethyl or naphthylmethyl,
(g) an alkenyl group preferably having 2–18 carbon atoms, more preferably 2–10 carbon atoms, such as vinyl, propenyl or 3-butenyl and (h) a silyl group which may have 1–3 substituents such as a hydrocarbyl group having 1–18 carbon atoms, preferably 1–8 carbon atoms, such as an alkyl (e.g. methyl, ethyl, propyl, butyl or octyl), cycloalkyl (e.g. cyclohexyl), aryl (e.g. phenyl, tolyl, naphthyl) or aralkyl (e.g. benzyl, phenethyl or naphthylmethyl), and $R^4$ stands for (i) an alkylene group preferably having 1–20 carbon atoms, more preferably 1–10 carbon atoms, such as methylene or tetramethylene, or (j) a cycloalkylene group preferably having 5–18 carbon atoms, more preferably 5–10 carbon atoms, such as cyclopentylene or cyclohexylene.

Illustrative of suitable acetylene compounds are non-substituted acetylene, butyne, octyne, phenylacetylene, trimethylsilylacetylene, 1,8-nonadiyne, diethynylbenzene, hexynenitrile and cyclohexenylacetylene. It is without saying that the present invention is not limited to these acetylene compounds.

The above reaction is performed in the presence of a palladium complex catalyst.

Any known palladium complex catalyst may be used. Low valency palladium complexes, inclusive of zero-valent complexes, may be suitably used. Low valency palladium complexes having a tertiary phosphine or a tertiary phosphite as a ligand are especially suitably used.

In this case, a precursor substance which can form in situ a low valency palladium complex having a tertiary phosphine or a tertiary phosphite as a ligand during the reaction of the acetylene compound with the secondary phosphite may also be suitably used. For example, a palladium complex containing neither tertiary phosphine nor tertiary phosphite may be used in conjunction with a tertiary phosphine or a tertiary phosphite so that a low valency palladium complex having a tertiary phosphine or a tertiary phosphite as a ligand is formed in the reaction mixture. Further, a palladium complex containing a tertiary phosphine or tertiary phosphite may be used in conjunction with another tertiary phosphine or another tertiary phosphite.

A tertiary phosphine of the following formula may be suitably used as a ligand of the palladium complex catalyst:

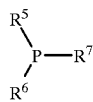

wherein $R^5$, $R^6$ and $R^7$ are each (k) an alkyl group preferably having 1–18 carbon atoms, more preferably 1–12 carbon atoms, such as methyl, ethyl, propyl, butyl, hexyl octyl or decyl, (l) a cycloalkyl group preferably having 4–6 carbon atoms, more preferably 5–6 carbon atoms, such as cyclopentyl or cyclohexyl, (m) an aryl group preferably having 6–14 carbon atoms, more preferably 6–10 carbon atoms, such as phenyl, naphthyl, substituted phenyl (e.g. tolyl or benzylphenyl) or substituted naphthyl (e.g. methylnaphthyl), or (n) an aralkyl group preferably having 6–13 carbon atoms, more preferably 6–10 carbon atoms, such as benzyl, phenethyl, phenylbenzyl or naphthylmethyl.

Examples of the tertiary phosphines include triphenylphosphine, tris(4-chlorophenyl)phosphine, tris(4-fluorophenyl)phosphine, tritolylphosphine, diphenylmethylphosphine, phenyldimethylphosphine, diphenylcyclohexylphosphine and phenyldicyclohexylphosphine.

Illustrative of suitable palladium complex catalysts containing a tertiary phosphine are tetrakis(triphenylphosphine) palladium, tris(triphenylphosphine)palladium, and ethylenebis-(triphenylphosphine)palladium.

A tertiary phosphite of the following formula may be suitably used as a ligand of the palladium complex catalyst:

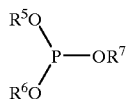

wherein $R^5$, $R^6$ and $R^7$ are as defined above.

Examples of the tertiary phosphites include trimethylphosphite and triphenylphosphite.

Palladium complex catalysts containing other ligands than tertiary phosphine or tertiary phosphite, such as bis(dibenzylideneacetone)palladium or palladium acetate, may also used, preferably in conjunction with the palladium complex catalyst containing tertiary phosphine or phosphite, for the purpose of the present invention.

The palladium complex catalyst is used in a catalytically effective amount and, generally, in an amount of up to 20 mole %, based on the acetylene compound. The acetylene compound and the phosphorothioate are generally used in a stoichiometric amount. However, the use of the acetylene compound or the phosphorothioate in a stoichiometrically excess amount does not adversely affect the desired reaction.

The reaction may be carried out with or without using a solvent. The solvent, when used, may be a hydrocarbon solvent or an ether solvent. The reaction is generally performed from room temperature to about 300° C., preferably 50–150° C. It is preferred that the reaction be carried out in an oxygen-free atmosphere, such as in the atmosphere of nitrogen, argon or methane.

After the termination of the reaction, the product can be separated by any known manner such as chromatography, distillation and recrystallization.

The following examples will further illustrate the present invention. The symbol Ph represents a phenyl group, t-Bu represents a t-butyl group, Me represents a methyl group and n-Bu represent a n-butyl group.

EXAMPLE 1

To 2 ml of toluene were added 2 mmol of 1-octyne, 2 mmol of PhSP(O) (OPh)$_2$ and 2 mol % of Pd(PPh$_3$)$_4$ (tetrakis(triphenylphosphine)palladium) and the mixture was reacted at 100° C. for 5 hours in the atmosphere of nitrogen. The reaction mixture was concentrated and separated by liquid chromatography to isolate diphenyl (Z)-2-phenylthio-1-octenylphosphonate with a yield of 92%. The physical properties of the novel product are given below.

$^1$H-NMR (CDCl$_3$): δ 7.15–7.41 (m, 15H), 5.81 (d, 1H $J_{H\text{-}P}$=17.3 Hz), 2.12 (t, 2H, J=7.6 Hz), 1.32–1.60 (m, 2H), 1.12–1.24 (m, 2H), 1.04–1.09 (m, 4H), 0.80 (t, 3H, J=7.0 Hz);

$^{13}$C-NMR (CDCl$_3$): δ 165.3, 150.6 ($J_{C\text{-}P}$=8.3 Hz), 134.7, 130.9, 129.6, 129.2, 129.1, 124.9, 120.7 ($J_{C\text{-}P}$=4.1 Hz), 110.6 ($J_{C\text{-}P}$=197.6 Hz), 38.2 ($J_{C\text{-}P}$=19.7 Hz), 31.3, 28.5, 28.2, 22.4, 14.0

$^{31}$P-NMR (CDCl$_3$): δ 8.3

IR (liquid film): 2932, 2860, 2593, 1491, 1272, 1216, 1193, 1164, 1071, 1025, 930, 754 cm$^{-1}$ Elementary analysis (as C$_{26}$H$_{29}$O$_3$PS)

calculated: C, 69.00; H, 6.46 measured: C, 69.06; H, 6.72

HRMS (EI, 70 eV):

calculated: 452.1575 measured: 452.1577

EXAMPLES 2–15

Example 1 was repeated in the same manner as described except that the acetylene compounds shown below were each used in lieu of 1-octyne to produce novel thioalkenylphosphonic acid esters shown below. The yield and physical properties of the esters are summarized below.

EXAMPLE 2

Acetylene compound:

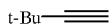

Product:

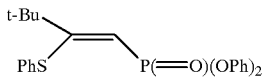

Yield: 65%
$^1$H-NMR (CDCl$_3$): δ 7.09–7.42 (m, 15H), 6.57 (d, 1H, J$_{H-P}$=17.6 Hz), 1.14 (s, 9H);
$^{31}$P-NMR (CDCl$_3$): δ 6–8
IR (liquid film): 2972, 1591, 1491, 1276, 1214, 1191, 1164, 1027, 926, 748 cm$^{-1}$
Elementary analysis (as C$_{24}$H$_{25}$O$_3$PS)
 calculated: C, 67.91; H, 5.94
 measured: C, 68.21; H, 6.14
HRMS (EI, 70 eV):
 calculated: 424.1262
 measured: 424.1172

PRODUCT OF EXAMPLE 3

Acetylene compound:

Product:

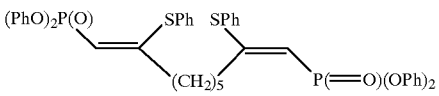

Yield: 90%
$^1$H-NMR (CDCl$_3$): δ 7.14–7.36 (m, 30H), 5.74 (d, 2H, J$_{H-P}$=17.4 Hz), 2.00 (t, 4H, J=7.0 Hz), 1.13–1.19 (m, 4H), 0.79–0.83 (m, 2H);
$^{31}$P-NMR (CDCl$_3$): δ 8.1
IR (liquid film): 2938, 1591, 1491, 1270, 1191, 1164, 1025, 928, 754 cm$^{-1}$
Elementary analysis (as C$_{45}$H$_{42}$O$_6$P$_2$S$_2$)
 calculated: C, 67.15; H, 5.26
 measured: C, 67.39; H, 5.41
FAB-MASS (EI, 70 eV): 804 (M+)

PRODUCT OF EXAMPLE 4

Acetylene compound:

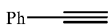

Product:

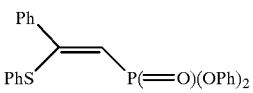

Yield: 87% (96/4)
$^1$H-NMR (CDCl$_3$): δ 6.97–7.41 (m, 20H), 6.12 (d, 1H, J$_{H-P}$=17.6 Hz);
$^{31}$P-NMR (CDCl$_3$): δ 7.3
IR (liquid film): 3062, 2928, 1593, 1555, 1,491, 1441, 1274, 1191, 1027, 926, 758, 690 cm$^{-1}$
Elementary analysis (as C$_{26}$H$_{21}$O$_3$PS):
 calculated: C, 70.26; H, 4.76
 measured: C, 70.29; H, 4.94
HRMS (EI, 70 eV):
 calculated: 444.0949
 measured: 444.0902

PRODUCT OF EXAMPLE 5

Acetylene compound:

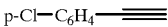

Product:

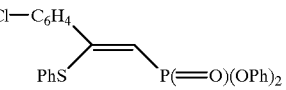

Yield: 71% (93/7)
$^1$H-NMR (C$_6$D$_6$): δ 7.08–7.33 (m, 19H), 6.19 (d, 1H, J$_{H-P}$=17.0 Hz);
$^{31}$P-NMR (CDCl$_3$): δ 6.8
IR (liquid film): 3,064, 1593, 1489, 1272, 1212, 1191, 1164, 1093, 1025, 938, 768 cm$^{-1}$
Elementary analysis (as C$_{26}$H$_{20}$ClO$_3$PS)
 calculated: C, 65.20; H, 4.21
 measured: C, 64.90; H, 4.27
HRMS (EI, 70 eV):
 calculated: 478.0559
 measured: 478.0489

PRODUCT OF EXAMPLE 6

Acetylene compound:

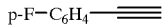

Product:

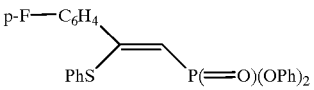

Yield: 69% (91/9)
$^1$H-NMR (CDCl$_3$): δ 6.83–7.34 (m, 19H), 6.16 (d, 1H, J$_{H-P}$=17.0 Hz);
$^{31}$P-NMR (CDCl$_3$): δ 7.1
IR (liquid film): 3066, 1597, 1491, 1274, 1212, 1191, 1162, 1025, 934, 797, 766 cm$^{-1}$
Elementary analysis (as C$_{26}$H$_{20}$FO$_3$PS)

calculated: C, 67.52; H, 4.36
measured: C, 67.51; H, 4.40
HRMS (EI, 70 eV):
  calculated: 462.0855
  measured: 462.0799

PRODUCT OF EXAMPLE 7

Acetylene compound:

Product:

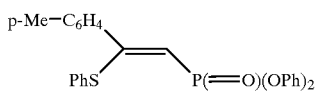

Yield: 89% (98/2)
$^1$H-NMR (CDCl$_3$): δ 6.97–7.33 (m, 19H), 6.20 (d, 1H, $J_{H-P}$=17.9 Hz), 2.22 (s, 3H);
$^{31}$P-NMR (CDCl$_3$): δ 7.6
IR (liquid film): 3062, 1593, 1551, 1491, 1274, 1212, 1191, 1164, 1025, 932, 766 cm$^{-1}$
Elementary analysis (as C$_{27}$H$_{23}$O$_3$PS)
  calculated: C, 70.73; H, 5.06
  measured: C, 70.65; H, 5.07
HRMS (EI, 70 eV):
  calculated: 458.1106
  measured: 458.1096

PRODUCT OF EXAMPLE 8

Acetylene compound:

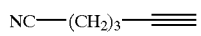

Product:

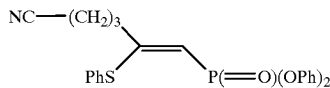

Yield: 84%
1H-NMR (CDCl$_3$): δ 7.06–7.50 (m, 15H), 5.88 (d, 1H, $J_{H-P}$=16.4 Hz), 2.30 (t, 2H, J=7.0 Hz), 2.04 (t, 2H, J=7.3 Hz), 1.63–1.69 (m, 2H);
$^{31}$P-NMR (CDCl$_3$): δ 6.9
IR (liquid film): 2928, 1591, 1491, 1270, 1191, 1164, 1025, 928, 754 cm$^{-1}$
Elementary analysis (as C$_{24}$H$_{22}$NO$_3$PS):
  calculated: C, 66.19; H, 5.09; N, 3.22
  measured: C, 66.32; H, 5.16; N, 3.14
HRMS (EI, 70 eV):
  calculated: 435.1058
  measured: 435.1035

PRODUCT OF EXAMPLE 9

Acetylene compound:

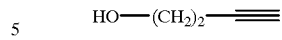

Product:

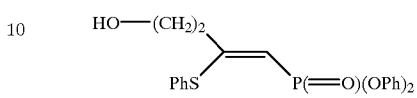

Yield: 89%
$^1$H-NMR (CDCl$_3$): δ 7.15–7.46 (m, 15H), 5.94 (d, 1H $J_{H-P}$=17.4 Hz), 3.55–3.68 (m, 2H), 2.39 (t, 2H, J=6.5 Hz), 1.82 (bs, 1H);
$^{31}$P-NMR (CDCl$_3$): δ 7.4
IR (liquid film): 3416, 3062, 2932, 1591, 1491, 1249, 1212, 1191, 936, 754 cm$^{-1}$
Elementary analysis (as C$_{22}$H$_{21}$O$_4$PS)
  calculated: C, 64.07; H, 5.13
  measured: C, 63.96; H, 5.16
HRMS (EI, 70 eV):
  calculated: 412.0898
  measured: 412.0902

PRODUCT OF EXAMPLE 10

Acetylene compound:

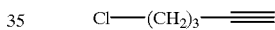

Product:

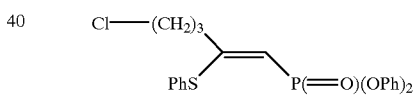

Yield: 85%
$^1$H-NMR (CDCl$_3$): δ 7.17–7.39 (m, 15H), 5.90 (d, 1H $J_{H-P}$=16.7 Hz), 3.26 (t, 2H, J=6.7 Hz), 2.33 (t, 2H, J=7.0 Hz), 1.77–1.79 (m, 2H);
$^{31}$P-NMR (CDCl$_3$): δ 7.6
IR (liquid film): 2962, 1591, 1491, 1270, 1214, 1191, 1025, 930, 752 cm$^{-1}$
Elementary analysis (as C$_{23}$H$_{22}$ClO$_3$PS)
  calculated: C, 62.09; H, 4.98
  measured: C, 62.44; H, 5.06
HRMS (EI, 70 eV):
  calculated: 444.0716
  measured: 444.0698

PRODUCT OF EXAMPLE 11

Acetylene compound:

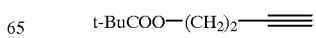

Product:

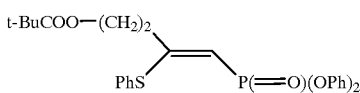

Yield: 68%
$^1$H-NMR (CDCl$_3$): δ 7.08–7.34 (m, 15H), 5.85 (d, 1H $J_{H-P}$=16.7 Hz), 3.97 (t, 2H, J=7.0 Hz), 2.41 (t, 2H, J=7.0 Hz), 1.04 (s, 9H);
$^{31}$P-NMR (CDCl$_3$): δ 6.9
IR (liquid film): 2976, 1729, 1591, 1491, 1280, 1214, 1191, 1162, 932, 768 cm$^{-1}$
Elementary analysis (as C$_{27}$H$_{29}$O$_5$PS)
    calculated: C, 65.31; H, 5.89
    measured: C, 65.66; H, 6.14
HRMS (EI, 70 eV):
    calculated: 496.1473
    measured: 496.1425

PRODUCT OF EXAMPLE 12

Acetylene compound:

Product:

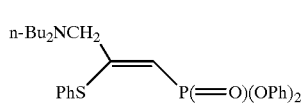

Yield: 91%
$^1$H-NMR (CDCl$_3$): δ 7.10–7.41 (m, 15H), 6.09 (bs, 1H), 6.04 (d, 1H, $J_{H-P}$=16.6 Hz), 1.92–1.97 (m, 4H), 1.31–1.34 (m, 4H);
$^{31}$P-NMR (CDCl$_3$): δ 8.6
IR (liquid film): 3062, 2934, 1593, 1551, 1491, 1274, 1214, 1191, 1164, 1027, 928, 766 cm$^{-1}$
Elementary analysis (as C$_{26}$H$_{25}$O$_3$PS)
    calculated: C, 69.62; H, 5.62
    measured: C, 69.58; H, 5.80
HRMS (EI, 70 eV):
    calculated: 448.1262
    measured: 448.1213

PRODUCT OF EXAMPLE 13

Acetylene compound:

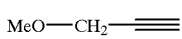

Product:

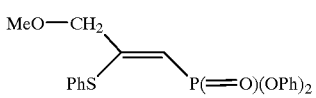

Yield: 88%
$^1$H-NMR (CDCl$_3$): δ 7.07–7.36 (m, 15H), 6.16 (d, 1H $J_{H-P}$=17.7 Hz), 3.67 (s, 2H), 3.11 (s, 3H);
$^{31}$P-NMR (CDCl$_3$): δ 8.6
IR (liquid film): 3046, 2934, 1591, 1491, 1274, 1214, 1191, 1120, 930, 756 cm$^{-1}$
Elementary analysis (as C$_{22}$H$_{21}$O$_4$PS)
    calculated: C, 64.07; H, 5.13
    measured: C, 64.35; H, 5.23
HRMS (EI, 70 eV):
    calculated: 412.0898
    measured: 412.0839

PRODUCT OF EXAMPLE 14

Acetylene compound:

Product:

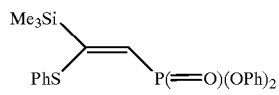

Yield: 94%
$^1$H-NMR (CDCl$_3$): δ 7.15–7.38 (m, 15H), 6.54 (d, 1H $J_{H-P}$=20.1 Hz), 2.88 (s, 2H), 2.19 (t, 4H, J 6.8 Hz), 1.14–1.15 (m, 8H), 0.82 (t, 6H, J=6.7 Hz);
$^{31}$P-NMR (CDCl$_3$): δ 10.0
IR (liquid film): 3064, 2960, 2866, 1593, 1491, 1274, 1216, 1193, 1164, 930, 768 cm$^{-1}$
Elementary analysis (as C$_{29}$H$_{36}$NO$_3$PS)
    calculated: C, 68.34; H, 7.12; N, 2.75
    measured: C, 68.90; H, 7.39; N, 2.67
HRMS (EI, 70 eV):
    calculated: 509.2154
    measured: 509.2124

PRODUCT OF EXAMPLE 15

Acetylene compound:

Me$_3$Si———≡

Product:

Me$_3$Si
  \
   ═
  /     \
PhS      P(═O)(OPh)$_2$

Yield: 60%
$^1$H-NMR (CDCl$_3$): δ 7.14–7.36 (m, 15H), 6.43 (d, 1H $J_{H-P}$=22.9 Hz), −0.08 (s, 9H);
$^{29}$Si-NMR (CDCl$_3$): δ 4.4 (Jp-si =26.2 Hz)
IR (liquid film): 3064, 2960, 1593, 1491, 1272, 1251, 1212, 1191, 1164, 930, 841, 793, 754 cm$^{-1}$
Elementary analysis (as C$_{23}$H$_{25}$O$_3$PSSi)
    calculated: C, 62.70; H, 5.72
    measured: C, 63.26; H, 5.60
HRMS (EI, 70 eV)
    calculated: 440.1031
    measured: 440.1035

What is claimed is:

1. A process for the preparation of a thioalkenylphosphonic acid ester of the following formula (I):

$$R^1C(SR^3)=CHP(=O)(OR^2)_2 \qquad (I)$$

wherein $R^1$ stands for a monovalent group selected from hydrogen atom, an alkyl group, a cycloalkyl group, a cycloalkenyl group, an aryl group, an aralkyl group, an alkenyl group and a silyl group, $R^2$ stands for an aryl group and $R^3$ stands for an aryl group, comprising reacting an acetylene compound of the following formula (II):

$$R^1C\equiv CH \qquad (II)$$

wherein $R^1$ is as defined above, with a phosphorothioate of the following formula (III):

$$(R^2O)_2P(=O)SR^3 \qquad (III)$$

wherein $R^2$ and $R^3$ are as defined above, in the presence of a palladium complex catalyst.

2. A process for the preparation of a bis(thioalkenyl) phosphonic acid ester of the following formula (IV):

$$[P(=O)(OR^2)_2]CH=C(SR^3)-R^4-C(SR^3)=CH[P(=O)(OR^2)_2] \qquad (IV)$$

wherein $R^2$ stands for an aryl group, $R^3$ stands for an aryl group and $R^4$ stands for an alkylene group or a cycloalkylene group, comprising reacting an acetylene compound of the following formula (II):

$$HC\equiv C-R^4-C\equiv CH \qquad (V)$$

wherein $R^4$ is as defined above, with a phosphorothioate of the following formula (III):

$$(R^2O)_2P(=O)SR^3 \qquad (III)$$

wherein $R^2$ and $R^3$ are as defined above, in the presence of a palladium complex catalyst.

3. A thioalkenylphosphonic acid ester of the following formula (I):

$$R^1C(SR)=CHP(=O)(OR^2)_2 \qquad (I)$$

wherein $R^1$ stands for a monovalent group selected from hydrogen atom, an alkyl group, a cycloalkyl group, a cycloalkenyl group, an aryl group, an aralkyl group, an alkenyl group and a silyl group and $R^2$ stands for an aryl group and $R^3$ stands for an aryl group.

4. A bis(thioalkenyl)phosphonic acid ester of the following formula (IV):

$$[P(=O)(OR^2)_2]CH=C(SR^3)-R^4-C(SR^3)=CH[P(=O)(OR^2)_2] \qquad (IV)$$

wherein $R^2$ stands for an aryl group, $R^3$ stands for an aryl group and $R^4$ stands for an alkylene group or a cycloalkylene group.

* * * * *

UNITED STATES PATENT AND TRADEMARK OFFICE
CERTIFICATE OF CORRECTION

PATENT NO. : 6,191,298 B1
DATED : February 20, 2001
INVENTOR(S) : Han et al.

It is certified that error appears in the above-identified patent and that said Letters Patent is hereby corrected as shown below:

Title page,
Item [73], Assignee Agency of Industrial Science and Technology" should read -- --[73] Assignee: Secretary of Agency of Industrial Science and Technology --.

Column 1,
Line 60, "-R-C(SR$^3$)" should read -- - R$^4$-C(SR$^3$) --.

Column 2,
Line 20, "R$^4$" should read -- R$^2$ --; and
Line 21, "R" should read -- R$^4$ --.

Column 4,
Line 57, at the end of the line insert a colon ":".

Column 5,
Line 22, "6-8" should read -- 6.8 --;
Line 25, at the end of the line insert a colon ":"; and
Line 55, at the end of the line insert a colon ":".

Column 6,
Line 40, at the end of the line insert a colon ":";
Line 67, at the end of the line insert a colon ":". and Column 7,
Line 30, at the end of the line insert a colon ":".

Column 8,
Line 22, at the end of the line insert a colon ":"; and
Line 52, at the end of the line insert a colon ":".

Column 9,
Line 15, at the end of the line insert a colon ":"; and
Line 46, at the end of the line insert a colon ":".

Column 10,
Line 7, at the end of the line insert a colon ":".
Line 30, "J 6.8" should read -- J=6.8 --;
Line 35, at the end of the line insert a colon ":";
Line 61, at the end of the line insert a colon ":"; and
Line 65, at the end of the line insert a colon ":".

UNITED STATES PATENT AND TRADEMARK OFFICE
CERTIFICATE OF CORRECTION

PATENT NO. : 6,191,298 B1
DATED : February 20, 2001
INVENTOR(S) : Han et al.

It is certified that error appears in the above-identified patent and that said Letters Patent is hereby corrected as shown below:

Column 11,
Line 25, should read -- $[P(=O)(OR^2)_2]CH=C(SR^3)-R^4-C(SR^3)=CH[P=O)(OR^2)_2]$ (IV) --.

Column 12,
Line 12, "$R^1C(SR)=CHP(=OR^2)_2$" should read -- $R^1C(SR^3)=CHP(=O)(OR^2)_2$ --.

Signed and Sealed this

Twenty-sixth Day of February, 2002

Attest:

*Attesting Officer*

JAMES E. ROGAN
*Director of the United States Patent and Trademark Office*